United States Patent [19]

Ciavattoni et al.

[11] 4,221,970
[45] Sep. 9, 1980

[54] PANORAMIC DENTAL X-RAY MACHINE EMPLOYING SELECTABLE MODE FILM DRIVE MECHANISM WITH SHIFTABLE CAM FOLLOWERS

[75] Inventors: Anthony Ciavattoni, Staten Island, N.Y.; John J. Flynn, Monmouth-Hazlet, N.J.; Theodore Weber, Jr., Elmsford, N.Y.

[73] Assignee: Pennwalt Corporation, Philadelphia, Pa.

[21] Appl. No.: 49,242

[22] Filed: Jun. 18, 1979

[51] Int. Cl.² ............................................. G03B 41/16
[52] U.S. Cl. ................................. 250/439 P; 250/468
[58] Field of Search ................ 250/439 P, 468, 439 R

[56] References Cited

U.S. PATENT DOCUMENTS 4,034,225  7/1977  Hudson ........................ 250/439 P
4,172,977  10/1979  Ciavattoni ..................... 250/439 P Primary Examiner—Craig E. Church

[57] ABSTRACT

Film drive mechanism for use with a panoramic X-ray machine which provides continuous and discontinuous radiographic images of dental arch areas of a shifting patient. The mechanism utilizes a linkage structure which carries a pair of shiftable cam followers which are separably engageable with cam members having working surfaces configured to advance or retard the speed of rotation of the linkage structure in accordance with mode of radiographing selected, i.e., continuous or discontinuous. A film drive shaft rotates in accordance with an output shaft connected to an output member of the cam-controlled rotating linkage structure which film drive shaft controls speed of rotation of a drum which has the X-ray film wrapped therearound.

11 Claims, 8 Drawing Figures

PANORAMIC DENTAL X-RAY MACHINE EMPLOYING SELECTABLE MODE FILM DRIVE MECHANISM WITH SHIFTABLE CAM FOLLOWERS

CROSS-REFERENCE TO OTHER RELATED PATENT APPLICATIONS

Reference is hereby made to Ser. No. 002,148, filed Jan. 9, 1979, for "Panoramic Dental X-Ray Machine X-Motion Drive" of R. Cushman et al., Ser. No. 025,127, filed Mar. 29, 1979, for "Link-Clutch Film Drive Mechanism for Panoramic Dental X-Ray Machine" of R. Cushman et al., both assigned to the assignee hereof.

STATEMENT OF THE INVENTION

The present invention relates to X-ray apparatus and more particularly concerns film drive mechanism which coordinates the speed of X-ray film travel with patient chair movement to provide undistorted continuous and discontinuous radiographs of dental arch areas.

BACKGROUND OF THE INVENTION

Prior art panoramic dental X-ray apparatus are well known in the art. Some provide a continuous image of the dental arch area and commonly employ an X-ray source and X-ray film supported on a rotatable carrying arm which orbits a patient situated in the beam path. The patient may remain stationary in the chair, or the chair may be transported in accordance with various X-Y type drive mechanism in order to simulate the generally elliptical shape of the human dental arch, as disclosed in U.S. Pat. No. 4,125,774, assigned to the present assignee. The continuous image radiograph provides the dentist with a panoramic view of the teeth and associated structures and is a useful diagnostic aid in many phases of dental practice.

Various other prior art apparatus provide a discontinuous, or split image panoramic radiograph which possesses certain advantages. Here, the dentist is provided with additional interpretive information since two distinctly different views of the incisors, or centrals area are provided. For example, in U.S. Pat. No. 3,045,118, apparatus is disclosed which automatically shifts the patient in order that the line of sight between the X-ray source and film bypasses the patient's spinal column and permits X-raying of the other half of the dental arch. Apparatus is also disclosed therein for continuously moving an X-ray source and extra-oral film holder about the patient.

In U.S. Pat. No. 2,798,958, means are disclosed for reorienting the patient after completion of one-half of the excursion cycle in order to relocate the center of the axis of rotation with respect to the patient's head prior to X-raying the other one-half of the dental arch in order to provide the discontinuous, or split radiograph images.

Regardless of the type radiographic image to be obtained, i.e., continuous or discontinuous, compensation is usually made for the fact that the curvature of the desired area of focus is generally not a true circle or ellipse. Thus, the rate of film travel must be varied in accordance with the chair shift or transport, and the rate of travel of the X-ray source about the patient's head in order that the radiological projections occupy a distance on the film equal to the linear distance of a curved structure being X-rayed, such as a typical dental arch.

The present invention discloses film drive mechanism which is readily adaptable for use with structure disclosed in cross-referenced patent application Ser. No. 002,148, for "Panoramic Dental X-Ray Machine X-Motion Drive", or with other suitable panoramic dental X-ray machines which provide either or both continuous and discontinuous radiographic images. With slight modification, the present invention may be substituted for the film drive mechanism disclosed in cross-referenced patent application Ser. No. 025,127, for "Link-Clutch Film Drive Mechanism for Panoramic Dental X-Ray Machine".

DETAILED DESCRIPTION OF THE INVENTION

Figure 1:
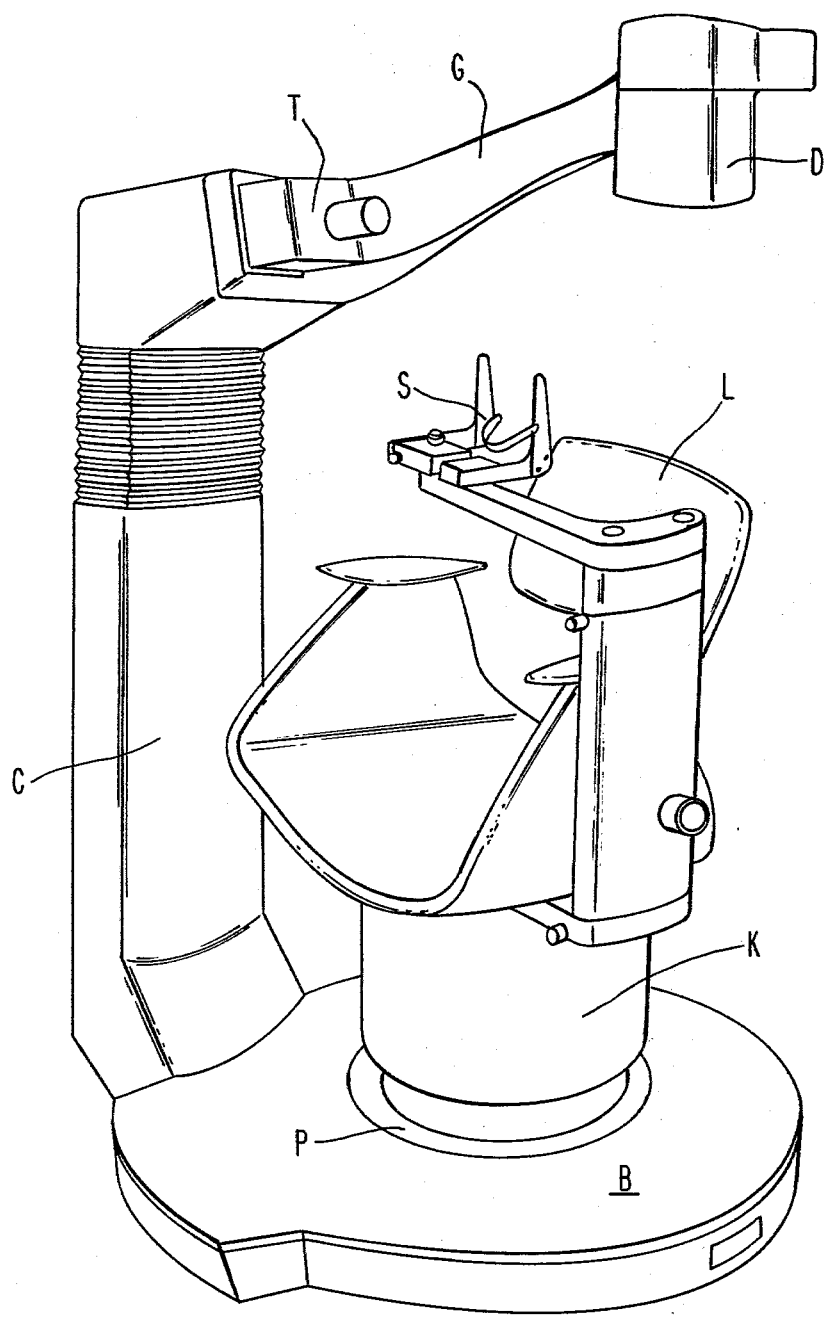
FIG. 1 is a perspective view of an assembled panoramic dental X-ray machine employing the film drive mechanism of the present invention.

Referring to FIG. 1 of the drawings, the panoramic X-ray machine comprises a base B having a stationary platform P disposed generally centrally thereof. Platform P supports a patient chair L including means S for supporting the chin and head of a patient. A column C is caused to rotate around chair L, the column carrying a tubehead T, a camera supporting arm G, and a camera assembly D which houses the film drive mechanism of the present invention. The chair shift and transport mechanism is located below chair L, within shroud K, the mechanism being bolted securely to stationary platform P. The excursion mechanism for causing column C to rotate around stationary platform P at a uniform and constant rate is supported and partially housed in base B.

Figure 2:
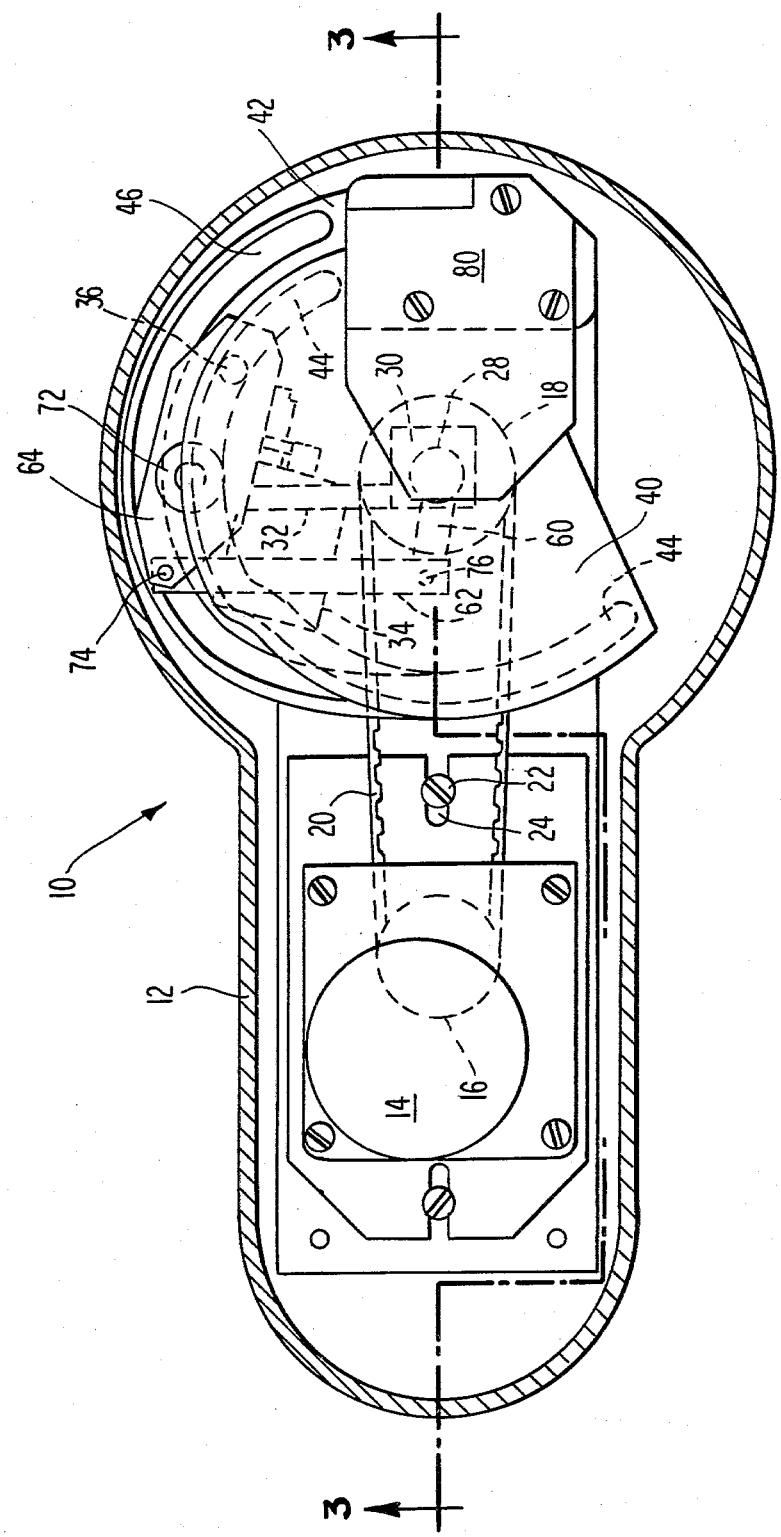
FIG. 2 is a plan view, partially sectioned, part in phantom, of the present film drive mechanism.
Figure 8:
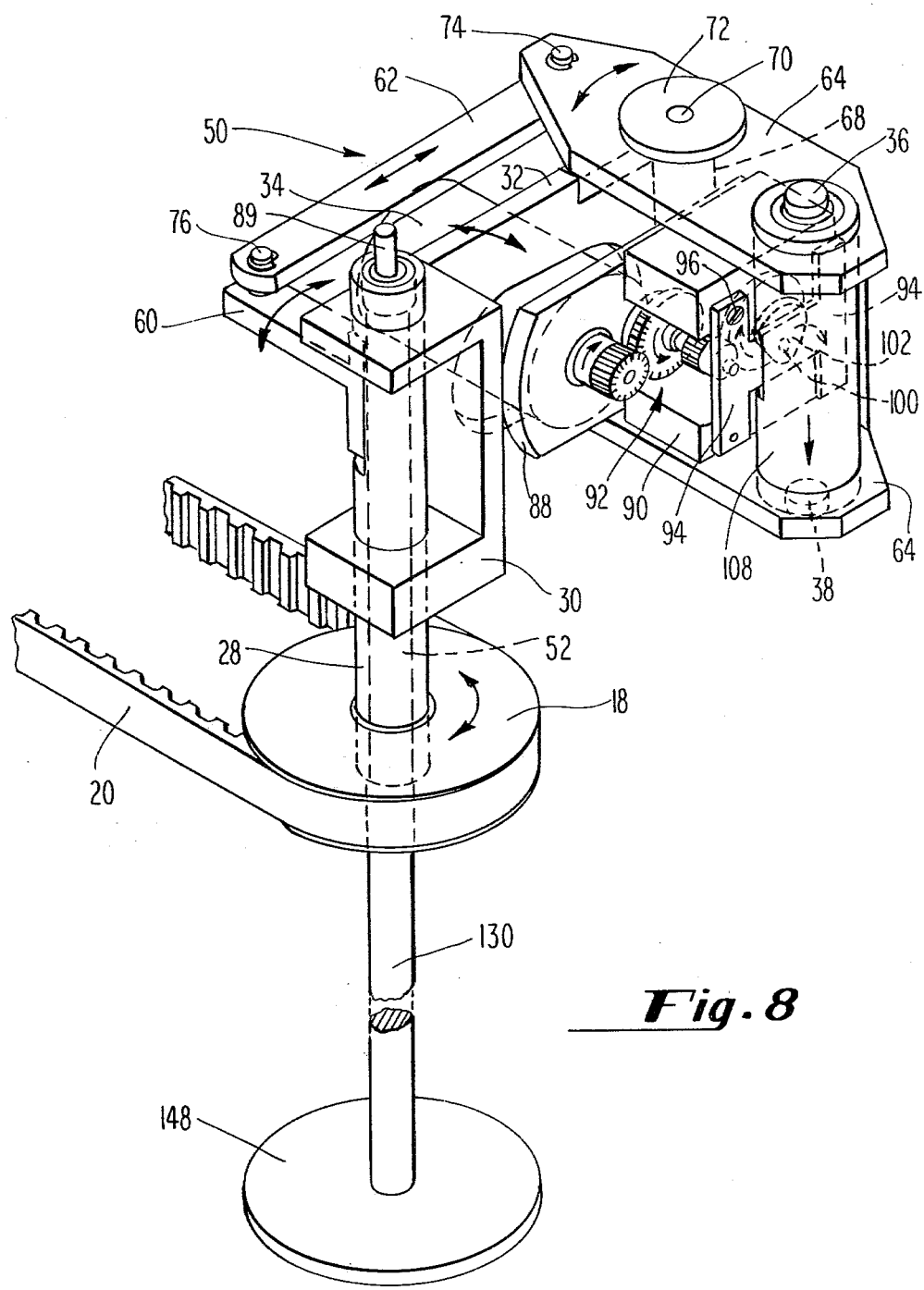
FIG. 8 is a perspective view of the film drive mechanism of the present invention, parts omitted for clarity.

Referring to FIGS. 2 and 8, film drive mechanism 10 may include a suitable housing 12 which contains synchronous, reversible, A.C. motor 14 having a 2 rpm output shaft. Motor 14 drives a pulley 16 causing input pulley 18 to rotate therewith by means of timing belt 20 operably connected therebetween. Control of tension on belt 20 is effected through cooperative action of screws 22 and slots 24.

Input pulley 18 is secured to hollow input or drive shaft 28 as is secured linkage drive 30 thereabove. Linkage drive 30 is provided with a laterally extending arm 32, such that rotation of shaft 28 causes a similar movement to linkage drive 30 and linkage drive arm 32. Arm 32 supports a reversible induction cam follower motor 34, appropriately geared down, which causes either one of two identical cam followers 36 and 38 to be individually and separably shifted, later described, for engagement with either a stationary plate cam 40, providing a discontinuous or split image of the dental arch area; or another stationary plate cam 42, providing a continuous image. Cam follower motor is ideally of the direct current type which lends itself readily to dynamic braking. "Split" cam 40 is disposed above cam follower 36, and "continuous" cam 42 is disposed below cam follower 38, each of the cams being provided with a working groove 44 and 46 respectively.

Each groove, when operably engaged by its respective cam follower, causes linkage structure 50 to rotate an output shaft 52 at non-constant speeds. An upper portion of output shaft 52 is concentrically disposed within hollow input or drive shaft 28. Non-constant speed of rotation of output shaft 52 governs the non-constant speed of rotation of the film drive shaft which similarly governs the speed of travel of the X-ray film.

Figure 6:
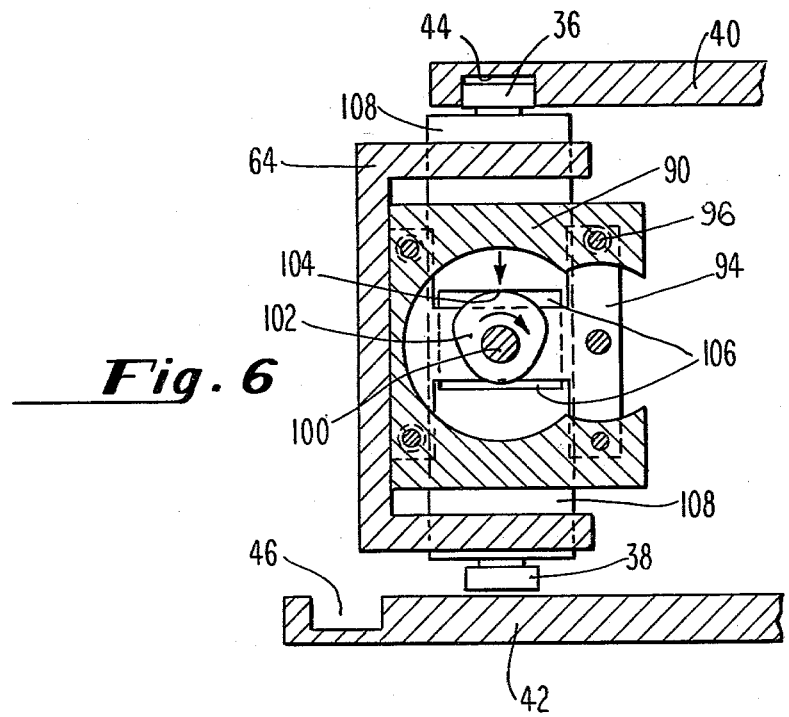

Linkage structure 50 includes an output member or link arm 60 secured to output shaft 52, connecting link 62, and a C-shaped rotating cam follower carrier 64 (clearly shown in FIG. 6).

Figure 5:
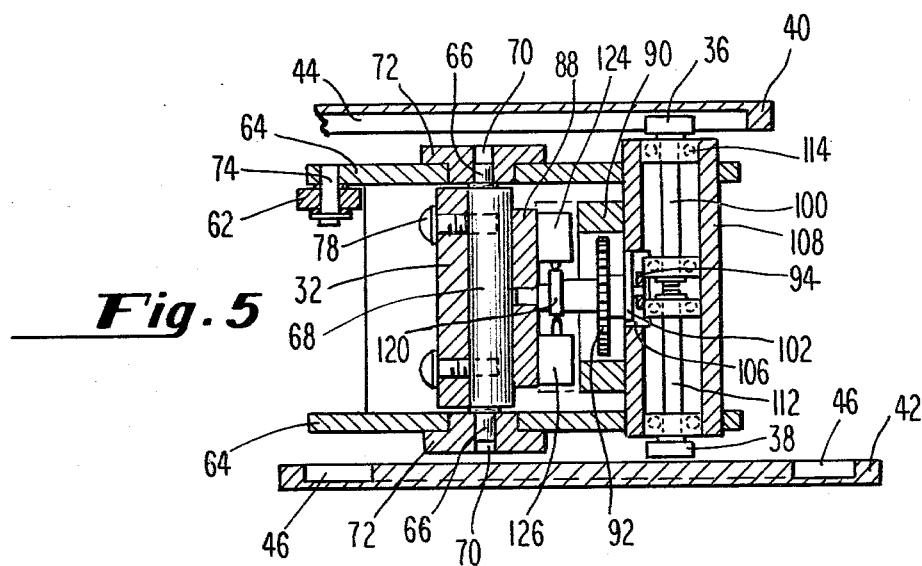
FIGS. 5, 6 and 7 are sectional views of FIG. 4 taken along lines 5—5, 6—6, 7—7 thereof respectively, looking in the direction of the arrows.

Carrier 64 is pivotable about two separate axes. At one, cam follower carrier 64 pivots about pivot pins 66, one of which extends axially from each of a spacer stud 68, disposed between the laterally extending arms of the C-shaped carrier 64. Pins 66 extend partially into orifices 70 of bushings 72 mounted in each arm of carrier 64 (FIG. 5).

At another axis, a pivot pin 74 permits rotating cam follower carrier 64 to pivot with respect to connecting link 62. Another pivot pin 76 provides the necessary pivotal action between connecting link 62 and link arm 60, the latter, as aforementioned, having an end affixed to output shaft 52.

Linkage drive arm 32 is fastened to stud 68 by screws 78. Thus, rotary movement of linkage drive arm 32 causes cam follower carrier 64 to move and simultaneously pivot about its two pivot points in accordance with predetermined complex patterns governed by the groove configuration of the particular cam groove being engaged by its respective cam follower, which cam followers are carried by carrier 64.

Figure 3:
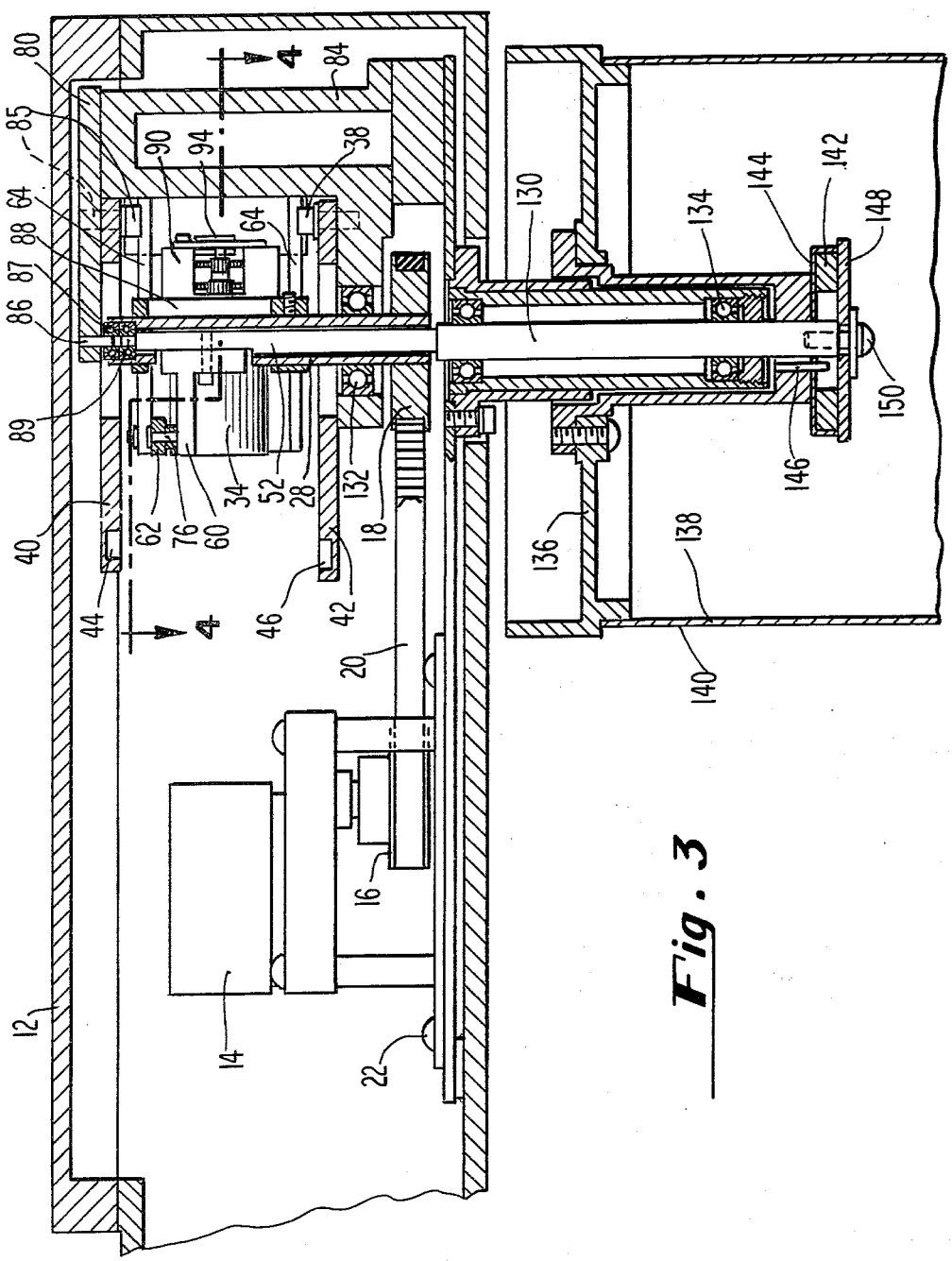
FIG. 3 is a sectional view of FIG. 2 taken along line 3—3 thereof.
Figure 4:
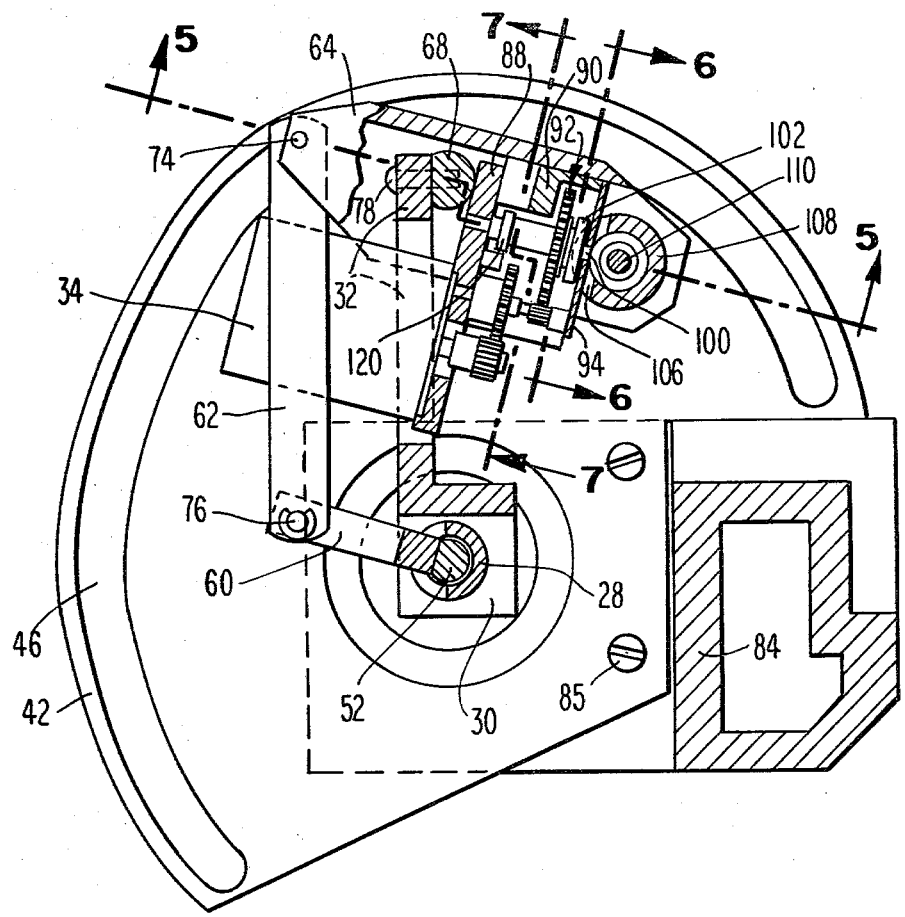
FIG. 4 is a sectional view taken along line 4—4 of FIG. 3.

Split cam 40 is supported by a member 80 which, in turn, is supported by a vertical support 84 (FIGS. 3 and 4). For purposes of easy access to the interior of the film drive mechanism, split cam 40 is hinged to support member 80. Screws 85 secure split cam 40 to support 80. Guide pin 86 is press fitted into support 80, which guide pin extends downwardly through a large central opening in split cam 40 for reception by a central orifice in bushing 87. Output shaft 52 is provided with a pin 89 which extends into the other end of the bushing orifice. When guide pin 86 is thus seated within the orifice, proper positioning of split cam 40 is insured.

Figure 7:
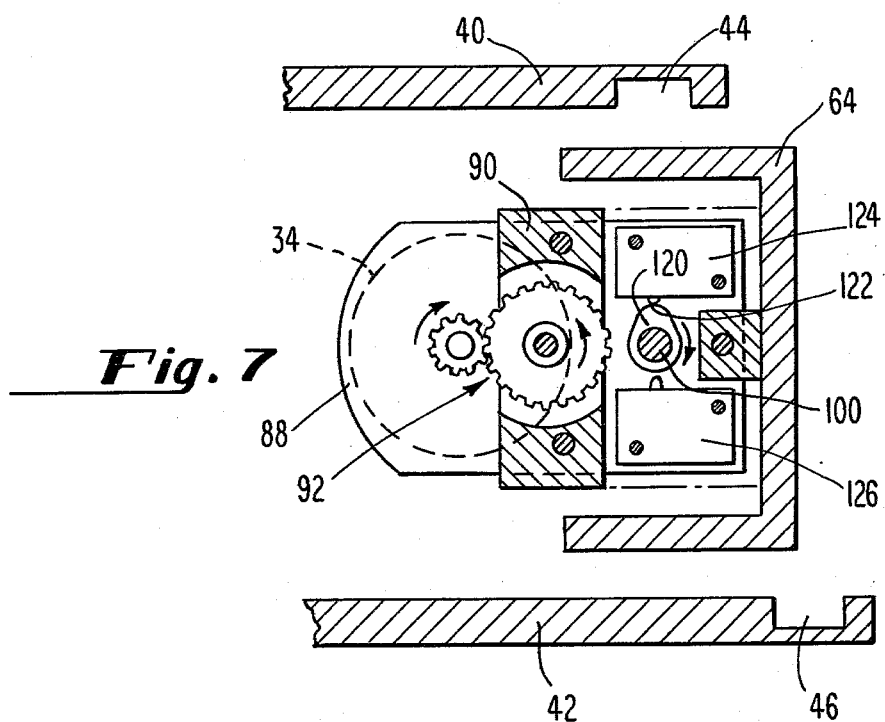

Referring to FIGS. 3, 4, 5 and 6, as well as to FIGS. 2 and 7, structure for effecting selection of continuous or split mode of radiographing the patient's dental arch is described below.

Cam follower motor 34 is carried by carrier 64 by means of a support plate 88 affixed thereto. Plate 88 is supported by a gear box 90 containing reduction gears 92. An H-plate 94 (FIGS. 6 and 8) is secured to gear box 90 by screws 96. Gear box 90 and support plate 88 are connected to cam follower carrier 64 but not to stud 68. H-plate 94 supports shafts of gear members 92 in the usual manner as well as selector cam shaft 100 which rotates selector cam 102. As clearly shown in FIG. 6, selector cam 102 is provided with a high-point 104 which, upon rotation of selector cam shaft 100, engages an upper edge of cut-out portion 106 (FIG. 5) provided in cam follower tube 108 to thus cause the tube to shift upwardly such that cam follower 36, carried by cam follower tube 108, engages groove 44 of the split cam. Once so engaged, motor 14 may then be actuated to start input shaft 28 rotating which effects rotation of linkage drive 30 and linkage drive arm 32, and consequently the entire linkage structure 50. Movement of linkage structure 50, in cooperation with the cam follower-groove arrangement, advances or retards the speed of rotation of output shaft 52 connected to link arm 60, and hence, the speed of rotation of the film drive shaft, later described.

The rate of change of the distances of grooves 44 and 46 from output shaft 52 as the respective cam follower rides in its respective groove determines the rate of change of speed of rotation of output shaft 52 and hence the film drive shaft. In the case of split or discontinuous images, for example, distance of groove 46 from output shaft 52 will control output shaft speeds, and hence, film drive speeds. To further clarify, if a cam follower rode in a groove which coincided with a circle having its center at the center of the output shaft, the speed of rotation of the output shaft, and hence, the film drive shaft, would be constant.

In panoramic dental X-ray machines of the assignee, film travel speed is slower when the cuspid-incisor area is radiographed as compared to the posterior regions of the mouth. Groove configuration to provide desired film travel speeds at various portions of a typical dental arch structure may be calculated by a skilled mathematician and are not described herein.

Alternatively, if a continuous radiographic image is desired, linkage structure 50 will be returned to its original starting position by switches and circuitry well known and not herein shown or described. Parenthetically, if another split or discontinuous image of the dental arch area is desired, the present invention is capable of radiographing in the other, or return direction.

When selector cam 102 is rotated 180° in a clockwise direction from its position illustrated in FIG. 6, through gearing 92 and cam follower motor 34, high-point 104 will engage a lower edge of cut-out portion 106 in tube 108 to urge the tube downwardly. Thus, cam follower 38 will be in engagement with groove 46 of cam 42 for providing the continuous radiographic images.

Cam followers 36 and 38 are rotatable on separate shafts 110 and 112 respectively within cam follower tube 108, although a single shaft would be equally operable. Bearings 114 permit the cam followers to rotate freely within their respective grooves.

Structure for effecting automatic cut-off of electric power to cam follower motor 34 after cam follower 36, for example, is seated within groove 44 is described below.

Selector cam shaft 100, in addition to mounting selector cam 102, mounts a switching cam 120 (FIG. 7) having a high point which alternately contacts normally closed limit switches 124 and 126. Thus, the seating or engagement of a cam follower within its respective groove is accompanied by an instant braking of cam follower motor 34 when highpoint 122 contacts the proper limit switch. Circuitry to accomplish the power cut-off is well within the skill of the art and is not shown or described herein.

In FIG. 3, film drive shaft 130 is shown affixed to output shaft 52, each shaft being rotatable within bearing members 132 and 134 respectively. Rotation of output shaft 52 rotates film drive shaft 130 which, in turn, rotates drum holder disc 136. Secured to drum holder disc 136 is a drum 138 having X-ray film 140 wrapped therearound. It is apparent therefore that rate and speed of travel of film 140 is governed by rotation of the output shafts 52.

In order to align the starting position of drum 138 and X-ray film 140, a magnetic slip clutch 142, suitably in the form of an annulus or separate pieces, is secured to flanged portion 144 by pinning 146 or other convenient means. Plate 148 is removably affixed to film drive shaft means 130 by screw 148. Alignment of the drum and film is achieved manually by rotating drum 138 to overcome the friction and attraction of magnetic slip clutch 142 to plate 148.

We claim:

1. In a panoramic dental X-ray machine for providing continuous and discontinuous radiographs of dental arch areas of a patient seated in a chair which travels during at least a portion of said continuous and discontinuous modes of radiographing, said X-ray machine comprising
   (a) a tubehead containing an X-ray source and means to power said source,
   (b) a camera assembly comprising a drum including X-ray film disposed therearound for activation by said X-ray source, said tubehead and said camera assembly rotating as a unit about said patient,
   (c) film drive means mounted within said camera assembly for rotating said drum and film at controlled rates of drive in accordance with travel of said chair and selected mode of radiographing while said tubehead and camera assembly circularly orbit said patient, the combination therewith of the improvement to said film drive means comprising
   a pair of stationary cams, one of said cams having a groove disposed therein for providing said continuous image and other of said cams having another groove disposed therein for providing said discontinuous image,
   rotatable link means carrying a pair of shiftable cam followers, said rotatable link means having an input member caused to be rotated at a constant speed and an output member rotating at a non-constant speed in accordance with rotatable engagement of a cam follower of one of said pair of shiftable cam followers within one of said grooves,
   said film drive means rotating in response to rotation of said output member of said link means.

2. The machine of claim 1 wherein said pair of stationary cams are spaced plate cams.

3. The machine of claim 2 wherein said grooves for providing said continuous and discontinuous images are disposed in opposing face-to-face surfaces of said plate cams.

4. The machine of claim 3 further characterized by
   a hollow drive shaft operably connected to said input member of said link means for rotation thereof,
   an output shaft concentrically disposed within said drive shaft,
   said output member of said link means secured to said output shaft for translating constant speed of rotation of said drive shaft into non-constant speeds of rotation of said output shaft by means of said link means and operable engagement of one of said cam followers with one of said grooves,
   said film drive means including a film drive shaft secured to said output shaft for rotation therewith.

5. The machine of claim 4 wherein said link comprises
   a rotatable cam follower carrying member pivotable about two separate axes, one of said axes being disposed at one end of said carrying member and other of said axes being disposed intermediate the ends of said carrying member,
   means for urging said carrying member in a rotary motion in accordance with rotary motion of said drive shaft,
   a connecting link pivotable to said carrying member at said one end thereof, and to said output member of said link means at one end thereof, said output member having its other end secured to said output shaft for translating constant speed of rotation of said drive shaft into non-constant speeds of rotation of said output shaft.

6. The machine of claim 5 wherein said means for urging said carrier member in a rotary motion about said drive shaft comprises said output member which further comprises
   a linkage drive member secured to said drive shaft, and
   a linkage drive arm extending from said linkage drive member and secured thereto.

7. The machine of claim 6 further characterized by said shiftable cam followers being carried at an end of said carrying member distal from said pivotal end thereof,
   a motor carried by said carrying member,
   means articulating with said motor for individually shifting one of said cam followers into engagement with one of said grooves of one of said plate cams and other of said cam followers into other of said grooves of said other plate cam.

8. The machine of claim 7 wherein said means articulating with said motor for individually shifting said cam followers comprises
   a cam follower tube mounted to said carrying member and adapted for movement towards either of said grooves, said tube having a cut-out portion intermediate its ends,
   a selector cam having a high point working surface rotatable within said cut-out portion, said selector cam being rotated by said motor a predetermined number of degrees whereby said high point working surface contacts an edge of said cut-out portion of selectively move said tube towards one of said grooves to provide engagement therewith of one of said cam followers.

9. The machine of claim 8 wherein said selector cam is rotatable on a cam shaft,
   a switching cam mounted proximally to said selector cam on said cam shaft, said switching cam having a high point working surface coincident with said high point working surface of said selector cam, said high point working surface of said switching cam activating electric means for braking movement of said tube upon proper engagement of one of said cam followers in its respective groove.

10. The machine of claim 4 wherein said drum is mounted for rotation with said film drive shaft and said X-ray film is wrapped around said drum.

11. The machine of claim 10 wherein magnetic means is disposed within said drum adjacent a lower portion of said film drive shaft for permitting alignment of said drum and X-ray film starting position.

* * * * *